United States Patent [19]

Meade et al.

[11] Patent Number: 5,272,254

[45] Date of Patent: Dec. 21, 1993

[54] PRODUCTION OF STREPTAVIDIN-LIKE POLYPEPTIDES

[75] Inventors: Harry M. Meade, Newton; Jeffrey L. Garwin, Bedford, both of Mass.

[73] Assignee: Biogen Inc., Cambridge, Mass.

[21] Appl. No.: 800,158

[22] Filed: Nov. 27, 1991

Related U.S. Application Data

[60] Division of Ser. No. 185,329, Apr. 21, 1988, Pat. No. 5,168,049, which is a continuation of Ser. No. 656,873, Oct. 2, 1984, abandoned.

[51] Int. Cl.$^5$ .................... C07K 13/00; C07K 7/00
[52] U.S. Cl. .................... 530/350; 530/300; 530/825
[58] Field of Search .................... 530/350, 825, 300

[56] References Cited

U.S. PATENT DOCUMENTS

| | | | |
|---|---|---|---|
| 4,338,397 | 7/1982 | Gilbert et al. | 435/69.1 |
| 4,411,994 | 10/1983 | Gilbert et al. | 435/69.7 |
| 4,839,293 | 6/1989 | Cantor et al. | |

FOREIGN PATENT DOCUMENTS

| | | |
|---|---|---|
| 0068867A2 | 1/1983 | European Pat. Off. |
| 2045251A | 10/1980 | United Kingdom |

OTHER PUBLICATIONS

Dailey et al. J. Biol. Chem. 253:8203-8209.
Berk, A. J. and P. A. Sharp, "Sizing and Mapping of Early Adenovirus mRNAs by Gel Electrophoresis of S1 Endonuclease-Digested Hybrids," Cell, 12, pp. 721–732 (Nov. 1977).
Bollen, A. et al., "Cloning and Expression in *Escherichia coli* of Full-Length Complementary DNA Coding for Human $\alpha_1$-Antitrypsin," DNA 2, pp. 255–264 (1983).
Grunstein, M. and D. S. Hogness, "Colony hybridization: A method for the isolation of cloned DNAs that contain a specific gene," Proc. Natl. Acad. Sci. USA, 72, pp. 3961–3965 (Oct. 1975).
Heppel, L. A., "Preparation of Cells of *Escherichia coli* with Altered Permeability," In *Methods In Enzymology*, 12B, pp. 841–847 (1968).
Hohn, B. and J. Collins, "A small cosmid for efficient cloning of large DNA fragments," Gene, 11, pp. 291–298 (1980).
Maniatis, T. et al., "Construction of Genomic Libraries in Cosmid Vectors," In *Molecular Cloning: A Laboratory Manual*, pp. 295–305 (1982).
Maxam, A. M. and W. Gilbert, "Sequencing End-Labeled DNA with Base-Specific Chemical Cleavage," In *Methods In Enzymology*, 65, pp. 499–560 (1980).
Pennica, D. et al., "Cloning and expression of human tissue-type plasminogen activator cDNA in *E. coli*," Nature, 301, pp. 214–221 (Jan. 1983).
Roberts, T. M. and G. D. Lauer, "Maximizing Gene Expression on a Plasmid Using Recombination *in Vitro*," In *Methods In Enzymology*, 68, pp. 473–482 (1979).
Towbin, H. et al., "Electrophoretic transfer of proteins from polyacrylamide gels to nitrocoellulose sheets: Procedure and some applications," Proc. Natl. Acad. Sci. USA, 76, pp. 4350–4354 (Sep. 1979).
Vieira, J. and J. Messing, "The pUC plasmids, an M13mp7-derived system for insertion mutagenesis and (List continued on next page.)

Primary Examiner—Robert A. Wax
Assistant Examiner—Gabriele E. Bugaisky
Attorney, Agent, or Firm—James F. Haley; Denise L. Loring

[57] ABSTRACT

DNA sequences, hybrid DNA sequences, recombinant DNA molecules and processes for producing streptavidin-like polypeptides and for producing fused proteins consisting of a streptavidin-like polypeptide joined end to end with another protein, polypeptide, peptide or amino acid. The DNA sequences, hybrid DNA sequences and recombinant DNA molecules of this invention are characterized in that they include DNA fragments that code for streptavidin-like polypeptides. These DNA sequences, hybrid DNA sequences and recombinant DNA molecules and the hosts transformed with them may be employed in the processes of this invention to produce streptavidin-like polypeptides and fused proteins.

5 Claims, 10 Drawing Sheets

OTHER PUBLICATIONS sequencing with synthetic universal primers," Gene, 19, pp. 259–268 (1982).

Villa-Komaroff, L. et al., "A bacterial clone synthesizing proinsulin," Proc. Natl. Acad. Sci. USA, 75, pp. 3727–3731 (Aug. 1978).

Chater, K. et al., "Gene Cloning in Streptomyces," In Current Topics in Microbiol. and Immunol., 96, pp. 69–75 (1982).

Katz, E. et al., "Cloning and Expression of the Tyrosinase Gene from Streptomyces antibioticus in Streptomyces lividans," J. General Microbiol., 129, pp. 2703–2714 (1983).

Stapley, E. O. et al., "Antibiotic MSD-235, I. Production by Streptomyces avidinii and Streptomyces lavendulae," Antimicrobial Agents and Chemotherapy, pp. 20–27 (1964).

Bayer, E. A. and M. Wilchek, "The Use of the Avidin-Biotin Complex as a Tool in Molecular Biology," In Methods of Biochem. Anal., 26, pp. 1–45 (1980).

Chaiet, L. and F. J. Wolf, "The Properties of Streptavidin, a Biotin-Binding Protein Produced by Streptomycetes," Arch. Biochem. Biophys., 106, pp. 1–5 (1964).

Cuatrecasas, P. and M. Wilchek, "Single-Step Purification of Avidin from Egg White by Affinity Chromatography on Biocytin-Sepharose Columns," Biochem. Biophys. Res. Commun., 33, pp. 235–239 (1968).

Finn, F. M. et al., "Hormone-Receptor studies with Avidin and Biotinylinsulin-Avidin Complexes," J. Biol. Chem., 255 pp. 5742–5746 (1980).

Heney, G. and G. A. Orr, "The Purification of Avidin and Its Derivatives on 2-Iminobiotin-6-aminohexyl-Sepharose 4B," Anal. Biochem., 114, pp. 92–96 (1981).

Hofmann, K. et al., "Iminobiotin affinity columns and their application to retrieval of streptavidin," Proc. Natl. Acad. Sci. USA 77, pp. 4666–4668 (Aug. 1980).

Korenman, S. G. and B. W. O'Malley, "Newer Methods of Avidin Assay," In Methods In Enzymology, 18A, pp. 427–430 (1970).

Orr, G. A., "The Use of the 2-Iminobiotin-Avidin Interaction for the Selective Retrieval of Labeled Plasma Membrane Components," J. Bio. Chem., 256, pp. 761–766 (Jan. 1981).

```
                    F                                                  BH
                    N           H         T   M                        SGXH
                    N           P         H   N                        PIMA
          F         A           I         I   L                        IAAE
          N         Q           F         I   I                        2133
    T     U    H                                                        //
    A     4    N
    Q     H    H
    1          1
    CCTCGACCATCGCCAAAGACACATGCCGCACTGTGTTTGTTCACCGACACCGTCAGGTGCACAGGCCGAGGTGCACAAACCTTGACGGGCG
301 ---------+---------+---------+---------+---------+---------+---------+---------+---------+ 400
    GGAGCTGGTAGGTCAAGAGACGGGTTTCTGTGTACGGCGTGACGACAAACAAGTGGCTGTGGCAGTCCACGTGCCGGCTCCAGTGTTTGGAACTGCCGC
    P  S  P  F  F  P  .  P  R  S  L  R  P  A  L  R  Q  T  P  P  R  T  R  R  P  P  R  S  R  P  P  R  P  A
    H  R  A  V  S  L  T  T  V  S  L  D  I  T  A  S  A  D  P  P  S  K  D  S  K  A  Q  V  S  A  A  E  A  G  I

BHF   H                    S                              H
              SINHHI                     HMNC                           IMHN  M  D          F
              SNUHHN                     PSCR              M            NSHL  B  P          N
     H        HPDAAP                     APIF              N            PTAA  O  N          U
     I        212111                     2111              L            1113  1  1          4
     N         //                        ///               1             //                 H
     H
     A
     1
    GGATACGGACGGGCACAGCCACAGAGCGCGCCCTCCGTCCCCGCGGGCAACAACAACTAGGGGAGTATTTTCGTGTCTCACATGCCAAGATCGTCGTTGCA
401 ---------+---------+---------+---------+---------+---------+---------+---------+---------+ 500
    CCTATGCCTGCCGTGTCGGTGTCGGTGTCGGCGCGGGAGGCAGGGCGGCCCGTTGTTGATCCCTCATAAAAAGCACAGAGTGTACGGTTCTAGCAGCAACGT
    C  A  R  S  S  L  Q     S
    M  R  K  I  V  V  A

H
                                    I   HH
                                    N   HA            B S              BSHHHMN
                                    H   AE   M   T    A H S  C         GFPAPSA
              T     A               P   AE   N   N    H S U  A  T  R   LIHEAPE
              A     Q               1   12   A   L    U A T  R  E  N  F 1113211
              Q     1                    3   E   Q    9 E N  F  L  Q  1  //
     B        1                          1   3   1    1 1 1  1  1  1
     B                                                6
     V
     1
    GCCATCGCCGTTCCCTGACCACGGTCTCGATTACGGCCAGGCCGCTTCGGCCAGCCCTTCCAAGGACTCGGAAGGCCCAGGTCCGAGCTGCAGCCGGCA
501 ---------+---------+---------+---------+---------+---------+---------+---------+---------+ 600
    CGGTAGCGGCAAGGGACTGGTGCCAGACTAATGCCGGTCAAGGCCGTCTTCCGGAAGCCGTCTCGAGCTTCCGAGAGGTTCCGGAGGGTCCAGGAGGCTCCGGCCGT
    P  S  F  F  P  .  P  R  S  L  R  P  A  L  R  Q  T  P  P  R  T  R  R  P  P  R  S  R  P  P  R  P  A
    H  R  A  V  S  L  T  T  V  S  L  D  I  T  A  S  A  D  P  P  S  K  D  S  K  A  Q  V  S  A  A  E  A  G  I
```

PRODUCTION OF STREPTAVIDIN-LIKE POLYPEPTIDES

This is a division, of application Ser. No. 07/185,329, filed Apr. 21, 1988, now U.S. Pat. No. 5,168,049, which is a continuation of U.S. patent application Ser. No. 656,783, filed Oct. 2, 1984; now abandoned.

TECHNICAL FIELD OF INVENTION

This invention relates to DNA sequences, recombinant DNA molecules and processes for producing streptavidin-like polypeptides and fragments thereof. More particularly, the invention relates to DNA sequences encoding streptavidin-like polypeptides and fragments thereof and recombinant DNA molecules containing those sequences for use in synthesizing those polypeptides and fragments in appropriate hosts, and in one embodiment secreting them and other products fused to them through the membrane of the host cell.

In another embodiment of this invention these DNA sequences and recombinant DNA molecules may be used to produce fusion proteins with desired proteins, polypeptides, peptides, and amino acids by linking them to DNA sequences that code for those products and expressing the resulting hybrid gene in an appropriate host. Depending on the particular construction and streptavidin DNA fragment employed, these fused proteins may be secreted through the membrane of the host in which they are made. Again, depending on the particular construction and streptavidin fragment employed they may also be more easily purified because of the exceptionally strong binding affinity of streptavidin for biotin and its derivatives.

BACKGROUND OF THE INVENTION

Streptavidin is an antibiotic produced by the bacteria *Streptomyces avidinii* and other *Streptomyces* species (E. O. Stapley et al., *Antimicrobial Agents and Chemotherapy* 1963, 20–27 (J. C. Sylvester ed. 1964)). It occurs naturally as a tetramer with a molecular weight of about 60,000 daltons. Streptavidin is characterized by its strong affinity for biotin and biotin derivatives and analogues. Each of the four identical subunits has a single biotin binding site (K. Hofmann et al., *Proc. Natl. Acad. Sci. USA* 77, 4666–68 (1980); L. Chaiet and F. J. Wolf, *Archives of Biochemistry and Biophysics* 106, 1–5 (1964)).

Because of its strong affinity for biotin, streptavidin has found widespread application, both commercially, and for applied and basic biomedical research, to study biotin-requiring enzymes and, when used in conjunction with biotinylated substances, to study the interactions between these substances and other products (K. Hofmann, supra; see also E. A. Bayer and M. Wilchek, *Methods of Biochemical Analysis* 26, 1–45 (1980); F. M. Finn et al., *J. Biol Chem.* 255, 5742–46 (1980)). Today, streptavidin is produced commercially by isolating it from the cell medium of *Streptomyces avidinii*. Purification of streptavidin from *Streptomyces avidinii* has resulted in very low yields of only 3–4 mg per liter of cell culture.

Recent advances in molecular biology have made it possible to produce large amounts of heterologous proteins in bacterial hosts. These include, for example, leukocyte interferon (S. Nagata et al., "Synthesis In *E. coli* Of A Polypeptide With Human Leukocyte Interferon Activity", *Nature* 284, 316–20 (1980)), antigens of human hepatitis B virus (C. J. Burrell et al., "Expression In *Escherichia coli* Of Hepatitis B Virus DNA Sequences Cloned In Plasmid pBR322," *Nature* 279, 43–47 (1979) and M. Pasek et al., "Hepatitis B Virus Genes And Their Expression In *E. coli*", *Nature* 282, 575–79 (1979)), SV40 t antigen (T. M. Roberts et al., "Synthesis Of Simian Virus 40 t Antigen In *Escherichia coli*", *Proc. Natl. Acad. Sci. USA* 76, 5596–5600 (1979)), and FMD viral antigens (H. Kupper et al., "Cloning Of cDNA Of Major Antigen Of Foot And Mouth Disease Virus And Expression In *E. coli*", *Nature* 289, 555–59 (1982)).

In general, these processes rely on the construction of recombinant DNA molecules characterized by a DNA sequence coding for the desired protein, polypeptide, peptide or amino acid operatively linked to an expression control sequence. Appropriate hosts are then transformed with these molecules to permit production of the desired product by fermentation. For DNA sequences, other than those prepared via chemical synthesis, the construction of such recombinant DNA molecules often comprises the-steps of producing a single-stranded DNA copy ("cDNA") of a messenger RNA ("mRNA") template for the desired product; converting the CDNA to double-stranded DNA and operatively linking the DNA to an appropriate expression control sequence in an appropriate cloning vehicle. The recombinant DNA molecule is then employed to transform an appropriate host. Such transformation may permit the host to produce the desired product when it is fermented under appropriate conditions.

A further improvement of the above technology has made it possible to excrete the selected protein, polypeptide, peptide or amino acid through the membrane of the host cell as it is produced by:

forming a hybrid gene consisting of a DNA sequence from an extracellular or periplasmic carrier protein that is excreted by the host, and a heterologous DNA fragment which codes for the selected protein, polypeptide or amino acid;

transforming the host with that hybrid gene operatively linked to an expression control sequence; and culturing the transformed host to synthesize and to secrete the selected protein, polypeptide, peptide or amino acid.

Such techniques are disclosed, for example, by L. Villa-Komaroff et al., "A Bacterial Clone Synthesizing Pro-Insulin," *Proc. Natl. Acad. Sci. USA* 75, 3727–31 (1978), and U.S. Pat. No. 4,411,994. However, any protein, polypeptide, peptide or amino acid made by this method, although separated from intracellular proteins and cell debris by secretion, must still be recovered from the cell medium or periplasmic space. This recovery generally involves a purification scheme that is less effective and less simple than desired. It also generally results in product losses.

SUMMARY OF THE INVENTION

The present invention solves the problems referred to above. It provides at least one DNA sequence characterized in that at least a portion thereof codes for a streptavidin-like polypeptide. The DNA sequences of this invention are selected from the group consisting of (a) SA304, SA307, SA324; (b) DNA sequences encoding polypeptides which hybridize to any of the foregoing DNA sequences and which code on expression for a streptavidin-like polypeptide; and (c) DNA sequences which code on expression for a polypeptide coded for on expression of any of the foregoing DNA sequences. These DNA sequences permit hosts transformed with them to produce streptavidin-like polypeptides. The present invention also provides at least one hybrid DNA sequence characterized in that at least a portion thereof codes for a fused protein consisting of a streptavidin-like polypeptide joined end to end with tissue plasminogen activator ("TPA"). The DNA sequences of this aspect of the invention are selected from the group consisting of (a) SAT9724 SAT7021; (b) DNA sequences encoding polypeptides which hybridize to any of the foregoing DNA sequences and which code on expression for the fused protein; and (c) DNA sequences which code on expression for a polypeptide coded for on expression of any of the foregoing DNA sequences.

It is accordingly possible to use the DNA sequences, recombinant DNA molecules, hosts and processes of this invention to avoid the prior low yields which have beset other known methods of streptavidin production. Accordingly, they enable large amounts of highly pure streptavidin-like polypeptides and their derivatives to be made available for diverse uses in the pharmaceutical and other industries.

In another embodiment, this invention provides a method of producing, and secreting through the membrane of the host cell, a selected protein, polypeptide, peptide or amino acid by expressing a hybrid DNA sequence consisting of a DNA sequence coding for a sufficient portion of a prestreptavidin-like polypeptide to cause the resulting fused protein to be secreted through the membrane of the host cell and a DNA sequence coding for the selected protein, polypeptide, peptide or amino acid. Upon expression of this hybrid DNA sequence, the fused protein that is expressed from this hybrid DNA sequence is secreted through the membrane of the host cell transformed by the hybrid DNA sequence. It may then be used as a fusion protein or cleaved by a variety of chemical, enzymatic and biological methods, to produce the desired protein, polypeptide, peptide or amino acid and a streptavidin-like polypeptide.

In still another embodiment, this invention provides a method for producing a fused protein that is purifiable by taking advantage of the binding affinity of streptavidin-like polypeptides for biotin and its derivaties or analogues. In this embodiment of the invention a hybrid DNA sequence consisting of a DNA sequence coding for a sufficient portion of a streptavidin-like polypeptide to cause the resulting fused protein to bind to biotin or its derivatives or analogues and a DNA sequence coding for the selected protein, polypeptide, peptide or amino acid is employed. Upon expression of this hybrid DNA sequence, the streptavidin moiety of the fused protein may be bound to biotin or one of its derivatives or analogues. Other secreted proteins or contaminants which do not bind to biotin can then be washed away and the fused protein eluted from the biotin. The selected protein, polypeptide, peptide or amino acid may then be used as a fusion protein or cleaved from the streptavidin-like polypeptide by conventional techniques, if necessary, and the streptavidin-like polypeptide and the selected protein, polypeptide, peptide or amino acid may then be collected separately.

In the most preferred embodiment of this invention, a fused protein is produced that is both secretable from the host cell in which it is made and purifiable by taking advantage of the binding affinity of streptavidin-like polypeptides for biotin and its derivatives or analogues. In this most preferred embodiment, a hybrid gene consisting of a DNA sequence coding for a sufficient portion of a prestreptavidin-like polypeptide to cause the resulting fused protein to be secreted through the membrane of the host cell and to cause the resulting fused protein to bind to biotin or its derivatives or analogues and a DNA sequence coding for the selected protein, polypeptide, peptide or amino acid is employed.

BRIEF DESCRIPTION OF THE DRAWINGS

FIG. 2(A-D) displays the nucleotide sequence of a portion of SA307 and the amino acid sequence of the regions of that portion coding for a streptavidin-like polypeptide. Line c of the amino acid sequence is the reading frame which is transcribed to produce a streptavidin-like polypeptide.

DETAILED DESCRIPTION OF THE INVENTION

Figure 1:
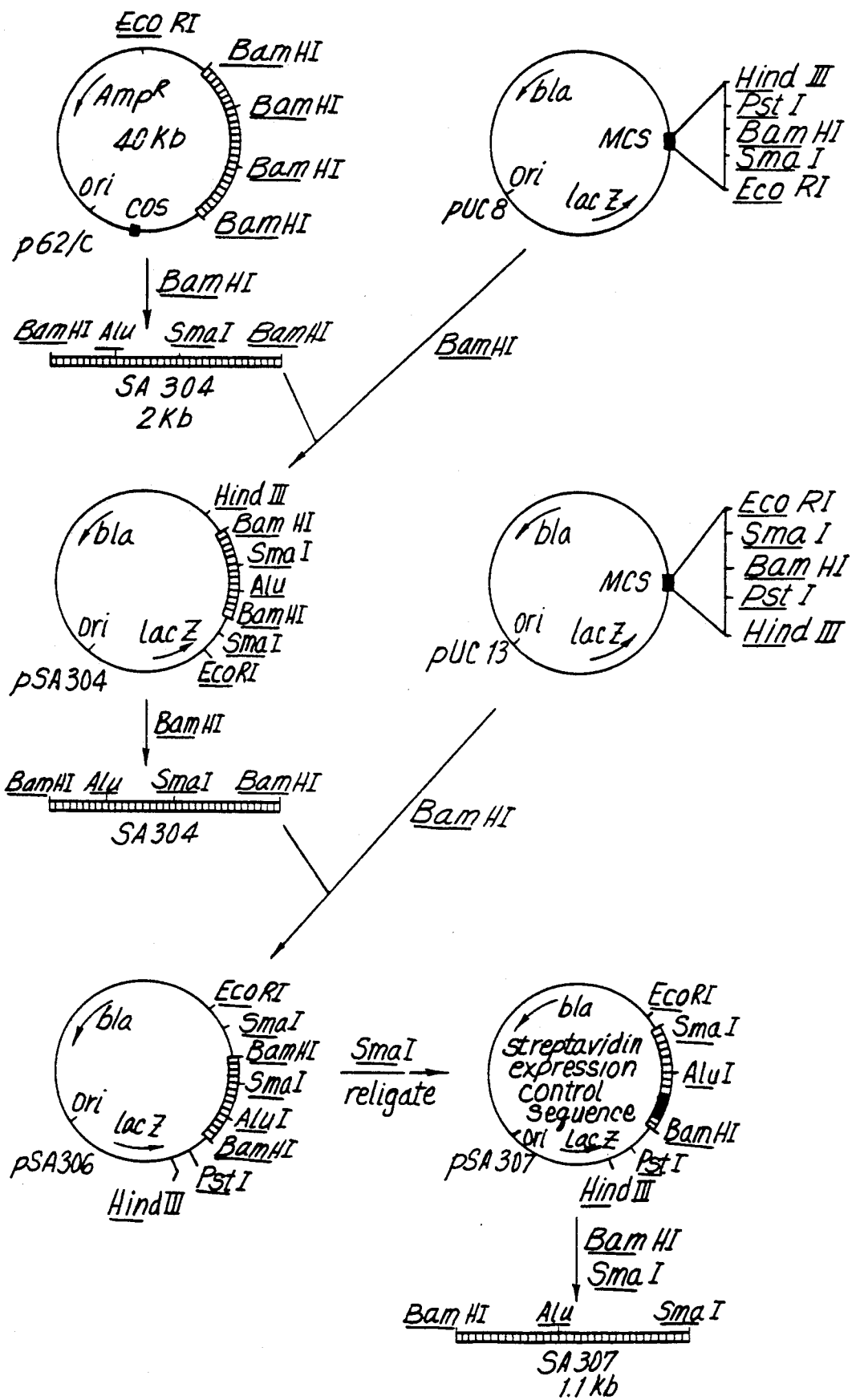
FIG. 1 is a schematic outline of one embodiment of making expression vectors pSA304 and pSA307, containing DNA sequences encoding the streptavidin-like polypeptides of this invention.

In accordance with this detailed description, the following definitions apply:

Protein—A polypeptide containing a linear series of more than fifty amino acids, e.g., tissue plasminogen activator, pro-insulin, serum albumin, human growth hormone, parathyroid hormone, and interferon.

Polypeptide—A linear series of amino acids connected one to the other by peptide bonds between the amino and carboxy groups of adjacent amino acids.

Precursor of a Protein or Polypeptide—A polypeptide or protein as synthesized within a host cell with a signal sequence, e.g., prestreptavidin, preproinsulin, preserum albumin, pregrowth hormone, preparathyroid hormone, and preinterferon. A mature polypeptide or protein is secreted through a host's cell membrane with the attendant loss or clipping (i.e., maturation) of the signal sequence of its precursor.

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("u").

DNA Sequence—A linear series of nucleotides connected one to the other by phosphodiester bonds between the 3' and 5' carbons of adjacent pentoses.

Codon—A DNA sequence of three nucleotides (a triplet) which encodes through messenger RNA ("mRNA") an amino acid, a translational start signal or a translational termination signal. For example, the nucleotide triplets TTA, TTG, CTT, CTC, CTA and CTG encode for the amino acid leucine ("Leu"), TAG, TAA and TGA are translational stop signals and ATG is a translational start signal.

Plasmid—A non-chromosomal double-stranded DNA sequence comprising an intact "replicon" such that the plasmid is replicated in a host cell. When the plasmid is placed within a unicellular host organism, the characteristics of that organism are changed or transformed as a result of the DNA of the plasmid. For example, a plasmid carrying the gene for tetracycline resistance (Tet®) transforms a host cell previously sensitive to tetracycline into one which is resistant to it. A host cell transformed by a plasmid is called a "transformant".

Phage or Bacteriophage—Bacterial virus, many of which include DNA sequences encapsidated in a protein envelope or coat ("capsid").

Cloning Vehicle—A plasmid, phage DNA or other DNA sequence which is able to replicate in a host cell, characterized by one or a small number of endonuclease recognition sites at which its DNA sequence may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is also known as a vector.

Host—An organism which, on transformation by a cloning vehicle, enables the cloning vehicle to replicate and to accomplish its other biological functions, e.g., the production of polypeptides or proteins through expression of the genes of a plasmid.

Cosmid—A plasmid containing the cohesive end ("cos") site of bacteriophage λ. Cosmids may, because of the presence of the cos site, be packaged into λ coat protein and used to infect an appropriate host. Because of their capacity for large fragments of foreign DNA, cosmids are useful as cloning vehicles.

Expression—The process undergone by a gene to produce a polypeptide or protein. It is a combination of transcription and translation.

Transcription—The process of producing mRNA from a gene.

Translation—The process of producing a protein or polypeptide from MRNA.

Promoter—The region of the DNA of a gene at which RNA polymerase binds and initiates transcription. A promoter is located before the ribosome binding site of the gene.

Ribosome Binding Site—The region of the DNA of a gene which codes for a site on MRNA which helps the MRNA bind to the ribosome, so that translation can begin. The ribosome binding site is located after the promoter and before the translational start signal of the gene.

Gene—A DNA sequence which encodes, as a template for MRNA, a sequence of amino acids characteristic of a specific protein, polypeptide or peptide.

Expression Control Sequence—A DNA sequence that controls and regulates expression of genes of the cloning vehicle when operatively linked to those genes.

Signal DNA Sequence—A DNA sequence within a gene for a polypeptide or protein which encodes, as a template for MRNA, a sequence of hydrophobic amino acids at the amino terminus of the polypeptide or protein, i.e., a "signal sequence" or "hydrophobic leader sequence" of the polypeptide or protein. A signal DNA sequence is located in a gene for a polypeptide or protein immediately before the DNA sequence coding for the mature protein as polypeptide and after the translational start signal (ATG) of the gene. A signal DNA sequence codes for the signal sequence of a polypeptide or protein, which (signal sequence) is characteristic of a precursor of the polypeptide or protein.

It is believed that only a portion of a signal sequence of a precursor of a protein or polypeptide is essential for the precursor of the protein or polypeptide to be transported through the cell membrane of a host and for the occurrence of proper clipping of the precursor's signal sequence to form the mature protein or polypeptide during secretion. Hence, the term "signal DNA sequence" means the DNA sequence which codes for the portion of the signal sequence essential to secretion and preferably to maturation of a precursor of a protein, polypeptide or peptide, produced within a host cell.

Streptavidin-like Polypeptide—A polypeptide which is substantially immunologically equivalent to natural streptavidin and is able to bind to biotin or biotin derivatives or analogues. This polypeptide may contain amino acids which are not part of natural streptavidin or may contain only a portion of natural streptavidin. The polypeptide may also not be identical to natural streptavidin because the host in which it is made may lack appropriate enzymes which may be required to transform the host-produced polypeptide to the structure of natural streptavidin.

THE HOST CELLS OF THIS INVENTION

Any of a large number of available and well-known host cells may be used in the host/expression vector combinations of this invention. The selection of a particular host is dependent upon a number of factors recognized by the art. These include, for example, compatibility with the chosen expression vector, toxicity to it of the proteins encoded for by the hybrid plasmid, ease of recovery of the desired protein, expression characteristics, biosafety and costs. A balance of these factors must be struck with the understanding that not all hosts may be equally effective for the expression of a particular DNA sequence in the expression vectors and methods of this invention.

Within these general guidelines, useful microbial hosts may include strains of E. coli, Pseudomonas, Bacillus, Streptomyces, yeast and other fungi, insect, plant or animal (including human) cells in culture, or other hosts known in the art.

Most preferably, the host used in this invention is a gram positive bacterium such as Streptomyces. Gram positive bacteria do not possess an outer cell wall. Therefore, an excreted protein is transported across the cell membrane directly into the cell medium. This characteristic eliminates the need to isolate the protein from the periplasmic space, as often required when gram negative bacteria, such as *E. coli*, are used as host cells for protein secretion systems. The protein may be purified, free of all cellular contaminants, directly from the cell medium. The preferred gram positive host cell strain is *Streptomyces lividans*.

THE EXPRESSION CONTROL SEQUENCES OF THIS INVENTION

In order to express the streptavidin DNA sequences or hybrid streptavidin-heterologous DNA sequences of this invention, those DNA sequences must be operatively linked to an expression control sequence. Methods of effecting this operative linking, either before or after the DNA sequence is inserted into the cloning vehicle, are well known.

Expression control sequences useful in this invention are also well known. They include the *E. coli lac* system, the *E. coli trp* system, the *E. coli β-lac* system, the TAC system, the TRC system, the major operator and promoter regions of bacteriophage phage λ, the control region of filmentoris single-stranded DNA phages, the expression control sequences of Streptomyces or other gram positive bacteria and other sequences known to control the expression of genes of prokaryotic or eukaryotic cells and their viruses or combinations thereof.

More preferably, expression control sequences operative in gram positive bacteria are used. Most preferably, Streptomyces expression control sequences are employed when Streptomyces host cells are used.

THE CLONING VEHICLES OF THIS INVENTION

In accordance with this invention, any cloning vehicle able to replicate in a host cell and having a restriction site into which DNA fragments can be inserted, may be used. The preferred cloning vehicles used in this invention are multicopy plasmids that are able to replicate in Streptomyces.

The specific location of the insertion site in the cloning vehicle into which the streptavidin DNA sequences or hybrid streptavidinheterologous DNA sequences of this invention are inserted, is not critical for making the selected protein, polypeptide, peptide or amino acid. In this regard, the cleavage site can be located anywhere in the cloning vehicle that does not interfere with its replication in the host cell.

Restriction enzymes used to create the desired cleavage site are well known. They include, for example, AraI, PstI, SalI, EcoRI, BamHI, HindIII, HincII and Sau3a. Methods for cleaving the cloning vehicles used in the methods of this invention at the desired restriction site and inserting into that site a DNA sequence are also well-known.

EXPRESSION OF DNA SEQUENCES ACCORDING TO THE METHODS OF THIS INVENTION

The methods of this invention may be employed to express DNA sequences coding for a streptavidin-like polypeptide or hybrid DNA sequences consisting of a DNA sequence coding for a portion of a streptavidin-like polypeptide and a DNA sequence coding for a desired eukaryotic, prokaryotic or viral protein, polypeptide, peptide or amino acid in a variety of ways.

In the embodiment of this invention in which it is desired to produce streptavidin-like polypeptides alone, the DNA sequence coding for the desired polypeptide is operatively-linked to an expression control sequence in a cloning vehicle. In such a construction, there should be a translational start signal immediately preceding the DNA sequence coding for the streptavidin-like polypeptide, if that sequence does not itself begin with a start signal. There also should be no stop codon between the start signal and the end of the DNA sequence coding for the streptavidin-like polypeptide. The resulting recombinant DNA molecule is then used to transform an appropriate host and the transformed host cultured under conventional fermentation conditions to produce the desired streptavidin-like polypeptide.

In a preferred embodiment of this aspect of the invention, a DNA sequence encoding a portion of a carrier protein, including a sufficient portion of the carrier protein signal sequence to cause the fused carrier protein-streptavidin-like polypeptide to be secreted from the cell in which it is made, resides between the translational start signal and the DNA sequence encoding the streptavidin-like polypeptide. More preferably only the carrier protein signal DNA sequence, without any of the DNA sequences coding for the carrier protein itself, is present between the translational start signal and the DNA sequences coding for the streptavidin-like polypeptide. Most preferably, the signal DNA sequence present between the translational start signal and the DNA sequences encoding a streptavidin-like polypeptide is the streptavidin signal DNA sequence, a sufficient portion of which is present to cause the streptavidin-like polypeptide to be secreted from the host cell.

In this manner, the streptavidin-like polypeptide is produced and secreted from the transformed host. Preferably, the signal sequence is cleaved from the streptavidin-like polypeptide or the fused carrier protein-streptavidin-like polypeptide during its secretion from the cell. In the embodiment where a portion of a carrier protein is fused to the streptavidin-like polypeptide, after production and isolation of the fused protein, it is preferable to cleave the streptavidin-like polypeptide from the carrier protein using known methods discussed infra.

In the embodiment of this invention in which it is desired to produce a non-streptavidin-like protein, polypeptide, peptide or amino acid using the methods of this invention, the DNA sequence coding for that product is linked downstream from and in the same reading frame as at least a portion of the DNA sequence coding for a streptavidin-like polypeptide to form a hybrid DNA sequence. The resulting hybrid DNA sequence is then operatively linked to an expression control sequence in a cloning vehicle. Again, in such a construction there should be a translational start signal immediately preceding the hybrid DNA sequence, if the hybrid DNA sequence does not itself begin with a start signal. There also should be no stop codon between the start signal and the end of the hybrid DNA sequence.

In various embodiments of this aspect of the invention, some or all of the DNA sequences encoding the carrier protein/carrier protein signal sequence/streptavidin signal sequence combinations described supra, reside between the translational start signal and the hybrid DNA sequence. In this manner a fused protein consisting of the streptavidin-like polypeptide joined end to end with the non-streptavidin-like protein, polypeptide, peptide or amino acid is produced and secreted from the transformed host. In another embodiment, the streptavidin signal DNA sequence is directly linked to the DNA sequence encoding the non-streptavidin-like protein, polypeptide, peptide or amino acid to allow secretion of the protein, polypeptide, peptide or amino acid from the host cell. In all the above embodiments, the signal sequence preferably is cleaved upon secretion from the host cell. In the embodiment in which a portion of a carrier protein is fused to the fused protein, it is preferable to cleave the fused protein from the carrier protein using known methods discussed infra after production and isolation of the fused protein.

The appropriate portion of the DNA sequence coding for a streptavidin-like polypeptide or prestreptavidin-like polypeptide employed is determined by a number of factors. These include the expression characteristics of the DNA sequence encoding the desired product, the ease of secretion of the desired product, the ultimate use to which the desired product is to be put, and whether secretion using the streptavidin sequences, purification using streptavidin binding or both are desired.

For example, if the desired product is to be secreted using the streptavidin signal sequence and purified using streptavidin binding to biotin or biotin derivatives or analogues, a sufficient portion of the streptavidin signal sequence to allow secretion, and a sufficient portion of the mature streptavidin coding sequence to allow binding to biotin or one of its derivatives or analogues is required.

It should also be understood that if the non-streptavidin-like protein, polypeptide, peptide or amino acid itself is required, the streptavidin-derived sequences may be removed after production, secretion, purification or any combination of them by a variety of means. For example, the fused protein may include a chemical or enzymatic cleavage site useful to separate the desired product from the streptavidin-like polypeptide. In another embodiment of this invention, such a cleavage site is built into the fused protein by constructing the hybrid DNA sequence so that it has one or more codons between the portion coding for the undesired part of the fused protein and the portion coding for the desired part. On expression, these codons produce the desired cleavage site.

Because streptavidin contains no methionine residues, a preferred means of cleaving the fused protein—provided the desired protein, polypeptide, peptide or amino acid also contains no methionine residues—is to construct the hybrid DNA sequence with an ATG codon (coding for methionine) between the DNA sequence encoding the streptavidin-like polypeptide and the DNA sequence encoding the desired product. The fused protein may then be cleaved at the lone methionine residue by treatment with cyanogen bromide. (See E. Gross, *Methods In Enzymology* 11, 238-55 (1967).)

Among the heterologous DNA sequences which are useful in this invention are those which code for animal and human hormones, such as any of the various IFN-α's, particularly α2, α5, α7, α8, IFN-β, IFN-γ, human insulin and growth hormone, bovine growth hormone, swine growth hormone and erythropoietin, human blood factors and tissue plasminogen activator, viral or bacterial antigens, such as the core or surface antigen of HBV or the antigens of FMDV and other useful polypeptides of prokaryotic, eukaryotic or viral origin. Preferably, the heterologous DNA fragment used also contains its gene's translational stop signal and most preferably a part of its 3' non-coding region.

PURIFICATION OF THE PRODUCTS OF THIS INVENTION

The more advantageous embodiments of this invention are those in which the products produced, either a streptavidin-like polypeptide or a fused protein having a sufficient portion of a streptavidin-like polypeptide to permit binding to biotin or one of its derivatives or analogues, are purified by binding to biotin or a biotin derivative or analogue. The unbound contaminants are then discarded and the desired product recovered from the biotin. Of course, biotin-binding can also be used to separate the streptavidin residue of a fused protein from the desired product after cleavage of the fused protein as described previously.

Preferably, the streptavidin-like polypeptides of this invention are purified using bioaffinity chromatography. Most preferably, the chromatography resin is formed by covalently binding imminobiotin, a biotin analogue, to agarose, or some other inert matrix (see Hofmann et al., supra; G. Heney and G. A. Orr, *Anal. Biochem.* 114, 92-96 (1981)).*

* Streptavidin binds so strongly to unmodified biotin-agarose resin that it can be eluted only under very harsh conditions (see P. Cuatrecasas and M. Wilchek, *Biochem. Biopays. Res. Commun.* 33, 235-39 (1968)). Therefore, biotin agarose is unsatisfactory for use in purifying streptavidin-like polypeptides. However, biotin-agarose or similar resin may be useful in purifying a fusion protein of a streptavidin-like polypeptide linked to a selected protein, polypeptide, peptide or amino acid, which, because of the presence of the selected protein, polypeptide, peptide or amino acid, has a lower affinity for biotin.

Streptavidin binds to imminobiotin at basic pH and is eluted at acidic pH in the presence of high concentrations of urea. Most preferably, the streptavidin-like polypeptide is applied to an imminobiotin-agarose column in 5 mM sodium carbonate buffer, pH 10.5, 0.5 M NaCl, and eluted with 50 mM sodium acetate buffer, pH 3.8, 1 M urea.

In order that this invention be more fully understood, the following example, for illustrative purposes only, is included herein.

EXAMPLE

PREPARATION OF A STREPTAVIDIN DNA PROBE

We determined the amino acid sequence of the first 38 N-terminal amino acids of commercial streptavidin (purchased from BRL). We then chemically synthesized a 14-base probe ("SA-1") corresponding to a portion of the amino terminus of streptavidin (trp-tyr-asn-gln-leu).* This DNA probe was used to screen the cosmid library, prepared as described below, for DNA sequences encoding streptavidin-like polypeptides.

* The SA-1 probe was 16-fold degenerate and consisted of the sequence:

```
AACATATTAGTTGA
   G   G   CA
```

PREPARATION OF AN S. AVIDINII COSMID LIBRARY

We cultured *S. avidinii* cells in YME media and isolated the bacterial DNA in a standard manner (K. F. Chater et al., *Current Topics In Micro. and Immunol.* 96, 69-75 (1982)). We then partially digested the DNA with Sau3A and size fractionated it by centrifugation through a salt gradient. We collected fragments larger than 20 kb for insertion into the cosmid pHC79.

The cosmid pHC79, sold commercially by Boehringer Mannheim, consists of a portion of the plasmid pBR322, including the gene coding for ampicillin resistance, and the "cos" region, coding for the complementary ends of bacteriophage lambda DNA (B. Hohn and J. Collins, Gene 11, 291-98 (1980)).

We linearized pHC79 with BamHI, which cleaves the plasmid at a single site and produces ends complementary to those of the Sau3A-digested DNA. We then ligated the *S. avidinii* fragments to the linearized pHC79. The resultant recombinant DNA molecules, comprising the *S. avidinii* cosmid library, were added to a lambda in vitro packaging extract (Amersham). We used the resulting lysate to transfect *E. coli* K-12 strain ED8767 by standard procedures (Maniatis et al., *Molecular Cloning, A Laboratory Manual*, 295-305 (Maniatis, Fritch and Sambrook, ed. 1982)).

SCREENING OF THE S. AVIDINII COSMID LIBRARY WITH THE SA-1 PROBE

To screen the above-described library for DNA sequences encoding streptavidin, we grew the transfected *E. coli* cells in LB medium supplemented with ampicillin (50 pg/ml) at 37° C. Because cosmid pHC79 includes the gene coding for ampicillin resistance, *E. coli* K-12 cells which contain pHC79 will grow in the presence of ampicillin, while K-12 cells which do not contain pHC79 will not be able to grow. Therefore, growth in ampicillin-containing medium permits selection of hosts containing pHC79.

We selected 2200 Amp ® colonies and picked them into individual wells of 96-well microtiter plates. We grew the selected cultures as before at 37° C. and printed them out onto nitrocellulose filters in an array using a 96-pronged fork. We then hybridized the colonies with the SA-1 probe, prepared as described above, at 30° C. in 6XSSC buffer, 0.1% SDS overnight, using the hybridization methods of Grüstein and Hogess, *Proc. Natl. Acad. Sci. USA* 72, 3961-65 (1975). one of the 2200 colonies contained DNA sequences which hybridized to the SA-1 probe (colony 62/c).

ISOLATION OF THE STREPTAVIDIN-RELATED DNA

We isolated the plasmid DNA from colony 62/c and reconfirmed its hybridization to the SA-1 probe in the same manner as above. The plasmid DNA (p62/c) contained an insert of *S. avidinii* DNA of approximately 40 kb at the BamHI site of pHC79. Referring now to FIG. 1, we digested this 40 kb fragment with BamHI and isolated a 2 kb fragment which also hybridized to SA-1. We designated this 2 kb fragment SA304. We then linearized plasmid pUCs (J. Viera and J. Messing, *Gene* 19, 259-68 (1982)) with BamHI, which cleaves at one site, downstream from the lac promoter. We ligated the linearized pUCs to SA304 in a conventional manner. This ligation produced a recombinant DNA molecule which we designated pSA304.

We found that *E. coli* cells transformed with pSA304 produced and secreted across the cell membrane streptavidin-like polypeptides. However, this production and secretion occurred only when SA304 was in an orientation such that it was operatively linked to the lac promoter present on pUCs. On the basis of these results we concluded that pSA304 contained the *E. coli* lac promoter operatively linked to and controlling expression of DNA sequences encoding a streptavidin-like polypeptide, including the signal DNA sequences.[*]

[*] We confirmed the presence of the streptavidin signal DNA sequence by nucleotide sequencing of SA307, infra. We further confirmed the presence of the *S. avidinii* streptavidin expression control sequence by S1 mapping described infra.

We confirmed the presence on SA304 of DNA sequences coding for a streptavidin-like polypeptide by sequencing portions of pSA304. The nucleotide sequence near nucleotide number 623 (Alu) (see FIG. 2), within the SA304 fragment, matched exactly that of the SA-1 probe. The nucleotide sequence also conformed to that predicted from the protein sequence of a 20 amino acid region of the streptavidin polypeptide downstream from the region corresponding to the SA-1 probe.

DETERMINING THE NUCLEOTIDE SEQUENCE OF THE STREPTAVIDIN-LIKE POLYPEPTIDE

Referring again to FIG. 1, in order to localize more precisely and sequence the DNA fragment encoding the streptavidin-like polypeptide, we treated pSA304 with BamHI. We reisolated fragment SA304 and ligated it to the plasmid pUC13 which had been linearized with BamHI.[*] We next restricted the resultant plasmid (pSA306) with SmaI and religated the large fragment, resulting in the loss of a 900 base pair fragment of SA304 to form plasmid pSA307. We then treated pSA307 with BamHI and SmaI and isolated a 1.1 Kb fragment ("SA307"). We sequenced this fragment using the method of Maxam and Gilbert, *Methods In Enzymology* 65, 499-560 (1980). The sequence (FIG. 2) indicates the presence of a DNA fragment coding for a streptavidin-like polypeptide between the ATG translational start signal at nucleotide number 480 and the TAG stop signal at nucleotide number 1030. The sequence also indicates the presence of a signal DNA sequence coding for a 35 amino acid signal sequence. We confirmed the presence of the

[*] Plasmid pUC13 is identical to pUCs except that the nucleotides immediately surrounding the BamHI site are in a different orientation and contain an additional restriction site (J. Viera and J. Messing, supra).

streptavidin expression control sequence by S1 mapping, described infra.

EXPRESSION OF STREPTAVIDIN-LIKE POLYPEPTIDES IN E. COLI

We employed pSA304 and pSA307 to transform *E. coli* K-12 cells using standard procedures.

We then prepared and tested cultures of these transformed organisms for the expression and secretion into the periplasmic space of streptavidin-like polypeptides by the immunological reactivity,[*] biotin-binding activity and amino acid sequence of the N-terminal end of the *E. coli*-produced polypeptide.

[*] We raised rabbit anti-streptavidin antibodies against commercially-available streptavidin which we repurified by P-150 gel filtration chromatography. The antiserum recognized the commercial streptavidin and streptavidin purified from *S. avidinii* cell medium, as judged by immunoblots of protein electrophoretically transferred from SDS-polyacrylamide gels to nitrocellulose sheets (see H. Towbin et al., *Proc. Natl. Acad. Sci. USA* 76, 4350-54 (1979)).

Figure 3:
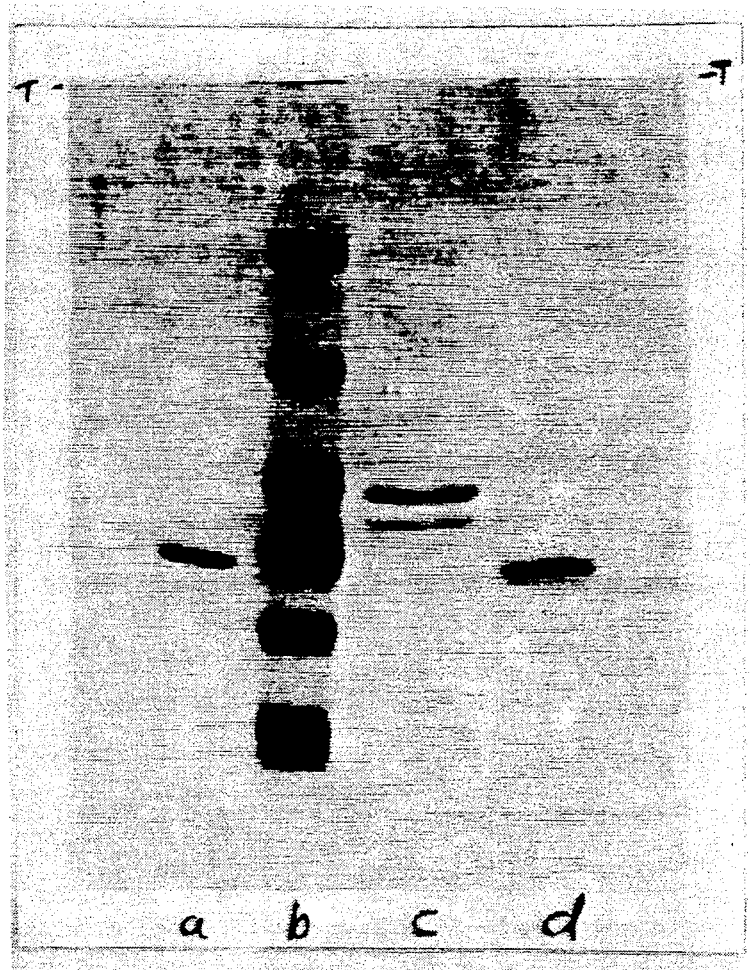
FIG. 3 depicts an SDS-polyacrylamide gel used to determine the apparent molecular weight of the streptavidin-like polypeptides of this invention. Lane a is a sample of repurified commercial streptavidin; lane b is a sample of protein standards with bands, reading from top to bottom, of 43Kd, 25.7Kd, 18.4 Kd, 14.3 Kd, 12.3 Kd, 6.2 Kd and 3.0 Kd; lane c is eco-avidin produced by expression of SA307 in *E. coli;* and lane d is a streptavidin-like polypeptide produced by expression of pSA3721 in *S. lividans.*

We cultured strain JM83 of *E. coli* K-12 cells transformed with pSA304 in LB medium containing 40 μg/ml ampicillin at 37° C. for approximately 18 hours. We isolated proteins from the periplasmic space using a cold osmotic shock technique (L. A. Heppel, *Methods In Enzymology* 126, 841-47 (1968)). Rabbit antiserum raised against the commercial streptavidin as described above recognized two major periplasmic polypeptides isolated from the osmotic shock fluid on western blots (see H. Towbin et al., supra). The larger of the two streptavidin-like polypeptides had an apparent molecular weight of about 17,500 daltons, determined by SDS-polyacrylamide gel electrophoresis, as compared with an apparent molecular weight of commercial streptavidin of 13,500 daltons (FIG. 3). The smaller of the two polypeptides had an apparent molecular weight of 15,000 daltons. The two streptavidin-like polypeptides co-eluted from iminobiotin-agarose chromatography columns. We next subjected the *E. coli*-produced streptavidin-like polypeptides ("eco-avidin major" and "eco-avidin minor") to P-150 gel filtration chromatography under non-denaturing conditions in 10 mM tris-HCl buffer, pH 8.0, 0.9% NaCl. The two eco-avidins migrated with an apparent molecular weight of approximately 88,000 daltons. This molecular weight is most consistent with a native tetrameric structure, similar to the naturally-occurring streptavidin.

We subjected the eco-avidins to biotinagarose and Sepharose CL-6B (unmodified agarose) column chromatography in the presence of 10 mM tris-HCl buffer, pH 8, 0.9% NaCl. The eco-avidins bound to the biotin-agarose, but did not bind to unmodified agarose. The eco-avidins also bound to columns of iminobiotin and displayed an elution pattern similar to that displayed by native streptavidin (see K. Hofmann et al., *Proc. Natl. Acad. Sci. USA* 77, 4666–68 (1980)).

We further confirmed the identity between naturally-occurring streptavidin and both forms of eco-avidin by sequencing the amino terminus of the eco-avidin polypeptides using an Applied Biosystems gas-phase amino acid sequenator. We separated the major and minor forms of the eco-avidin using SDS-polyacrylamide gel electrophoresis, electroeluted the polypeptides and separately determined the amino acid sequence of the amino terminus of each. The eco-avidins contained 13 amino acids at their amino terminus not present in naturally-occurring, mature streptavidin, followed by 12 amino acids identical to those of naturally-occurring streptavidin.* The protein sequence agreed precisely with that predicted from the nucleotide sequence of the corresponding region of SA307 and confirmed the cleavage in *E. coli* of a 22 amino acid fragment of the streptavidin signal sequence. Thus a 13 amino acid fragment of the streptavidin signal sequence remains in both forms of mature eco-avidin.

* Since both eco-avidin major and eco-avidin minor have the same amino terminus but different apparent molecular weights, they must differ at the carboxyl terminus. Upon hydroxylamine cleavage, eco-avidin major is converted to a form with an apparent molecular weight similar to that of eco-avidin minor. This is consistent with the inference that the two forms differ only at the carboxyl terminus.

We assayed the eco-avidin by its ability to bind radioactively-labelled biotin (see S. G. Korenman and B. W. O'Malley, *Meth. Enzymol.* 18A, 427–30 (1970)). The yield of purified eco-avidin was about 30 mg/liter of culture medium, a 7.5–10 fold increase over the yield of naturally-occurring streptavidin prepared from *S. avidinii*. *E. coli* cells transformed with pSA307 and assayed as above produced similar levels of streptavidin.

We confirmed in the same manner as with pSA304, supra, that the expression control sequence controlling expression of the streptavidin-like DNA fragments in pSA307-transformed *E. coli* cells was the *E. coli* lac promoter.

EXPRESSION OF STREPTAVIDIN-LIKE POLYPEPTIDES IN S. LIVIDANS

We have also cloned DNA sequences encoding a streptavidin-like polypeptide under the control of the streptavidin expression control sequence into an expression vector which is able to replicate in the gram positive bacteria *Streptomyces lividans*. Since pSA304 did not replicate in *S. lividans*, we made the cointegrant plasmid consisting of pSA304 and pIJ702. In this plasmid the streptavidin DNA sequences are operatively linked to both a lac promoter, located directly upstream from SA304, the inserted DNA sequence, and the streptavidin expression control sequence, present on SA304.

Figure 4:
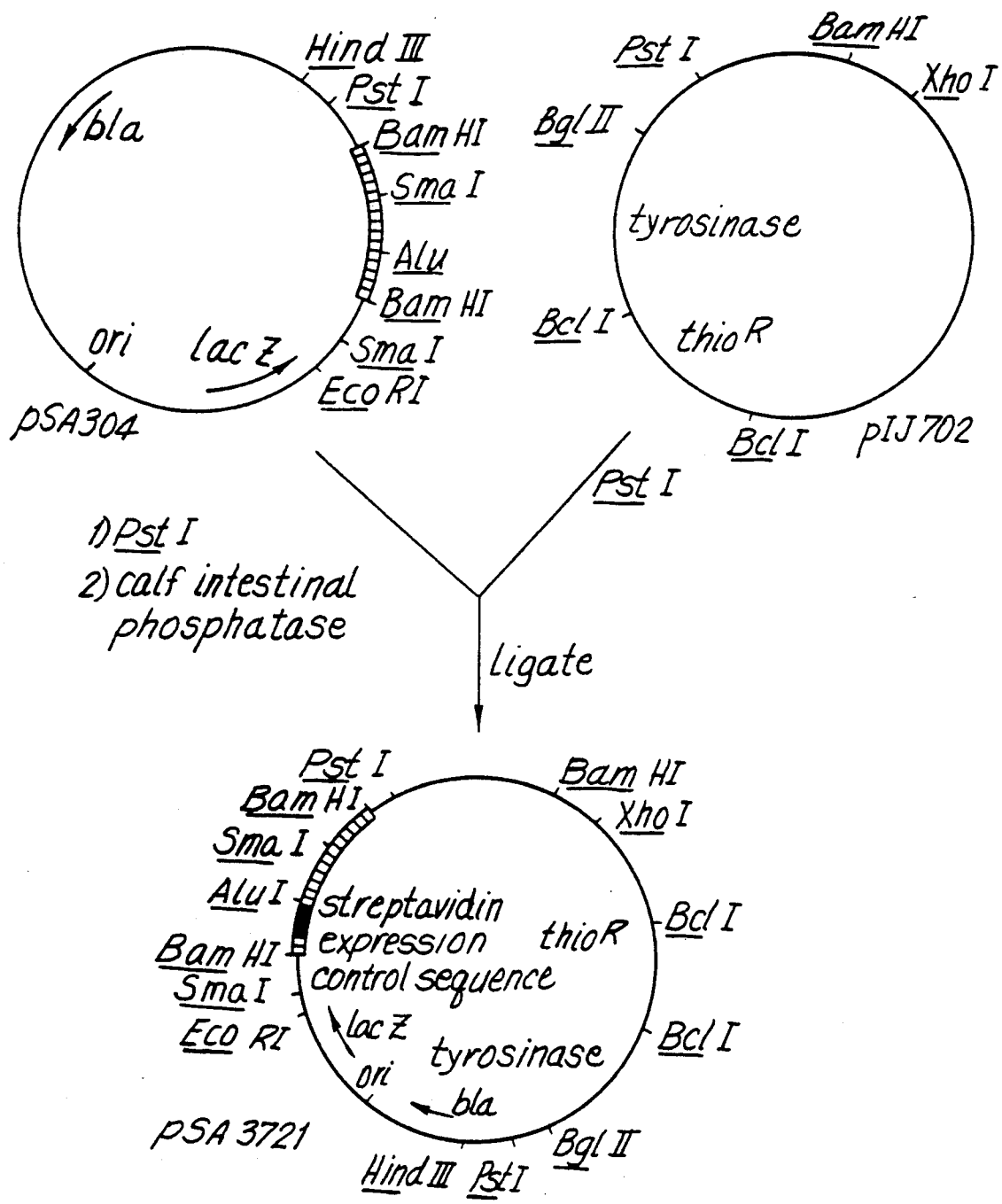
FIG. 4 is a schematic outline of another embodiment of making an expression vector containing DNA sequences encoding the streptavidin-like polypeptides of this invention.

Referring now to FIG. 4, we linearized pSA304 with PstI and treated the linearized plasmid with calf intestinal phosphatase to prevent recircularization. We next linearized pIJ702 (E. Katz et al., *J. Gen. Micro.* 129, 2703–14 (1983)) with PstI and ligated it to the linearized pSA304. The plasmid pIJ702 contains the Streptomyces marker gene for thiostrepton resistance as well as a replicon which allows growth in Streptomyces host cells.

We transformed *E. coli* JM83 cells with the ligation mixture and incubated as previously described in the presence of ampicillin. We isolated one AmpR colony containing the cointegrant plasmid pSA3721.

We isolated pSA3721 and used it to transform *Streptomyces lividans*. We selected for thiostrepton resistance and isolated eight colonies. We cultured each colony for up to eight days in R2YE medium containing 2 μg/ml thiostrepton in a baffled shaker flask at 30° C. We harvested the cells and culture medium at various times and, using the immunological and biotin binding assays described above, we tested for the production, and secretion into the cell medium, of a streptavidin-like polypeptide. We found that the transformed *S. lividans* produced, and secreted into the cell medium, a polypeptide which behaved in these assays identically to natural streptavidin. The level of production was approximately 250 mg. protein per liter of culture medium, an increase over *S. avidinii* production of about 60–80 fold. We confirmed that the streptavidin-like DNA sequences are under the control of the streptavidin expression control sequence present in the SA304 fragment by performing Si mapping experiments (A. J. Berk and P. A. Sharp, Cell 12, 721–32 (1977)) which show that the RNA transcript begins at the same site in *S. avidinii* and pSA3721.

In order to confirm that the streptavidin-like polypeptide produced and secreted by *S. lividans* was the result of expression of DNA fragments contained on the pSA3721 recombinant DNA molecule, we transformed *S. lividans* with pIJ702 alone under identical conditions and selected for thiostrepton resistance as above. None of the colonies isolated in this manner produced a protein with streptavidin-like activity as determined by any of the above-described assays.

PRODUCTION OF A FUSED PROTEIN OR POLYPEPTIDE

We next construct a hybrid DNA sequence by inserting into plasmid pSA307 DNA sequences encoding a selected protein, polypeptide, peptide or amino acid at a restriction site located at the end but before the translational stop signal of, and in the same reading frame as, the DNA sequences encoding the streptavidin-like polypeptide.

To effect this construction, for example, we use the DNA sequence encoding α-antitrypsin ("αAT"). We treat pULB1523 (A. Bollen et al., Gene 2, 255–64 (1983)) with BamHI and Pst and isolate the small DNA fragment which encodes all but the first two amino acids of aAT. We add a synthetic linker to the 5' end of this fragment to reconstruct the codons coding for the first two amino acids and to add an Nco restriction site at the 5' end of the fragment. We next linearize pSA304 by partial cleavage with HincII. We add Nco linkers to the linearized pSA304 and cleave with Nco to create cohesive ends. We next treat the linearized pSA304 with Pst. We select the fragment which has been cleaved by HincII and has an Nco linker only at nucleotide 994 of SA304. We ligate the DNA sequence encoding αAT to this DNA fragment to create a recombinant DNA molecule having the αAT inserted adjacent to and in the same reading frame as the DNA sequences encoding the streptavidin-like polypeptide.

We transform *E. coli* K12 cells with the resultant recombinant DNA molecule and culture the transformed host cells to produce and secrete through the host cell membrane, a fused polypeptide consisting of the streptavidin-like polypeptide joined end-to-end with the αAT.

Other DNA sequences are also available and may be used in the processes of this invention to produce a fused protein consisting of a streptavidin-like polypeptide joined to a selected protein, polypeptide, peptide or amino acid.

To construct a cloning vehicle which is able to replicate in Streptomyces and produce a fused streptavidin-like-αAT protein, we linearize the recombinant DNA molecule containing the hybrid DNA sequence with PstI and treat the linearized recombinant DNA molecule with calf intestinal phosphatase to prevent recircularization. We next ligate PstI-linearized pIJ702 to the linearized recombinant DNA molecule to create a cointegrant plasmid containing the hybrid streptavidin-αAT DNA sequence. We transform *S. lividans* cells with the cointegrant plasmid and culture the host cells to produce and secrete through the host cell membrane and into the cell medium a fused protein consisting of a streptavidin-like polypeptide joined end to end with αAT.

In another embodiment of this invention, we constructed a hybrid DNA sequence coding for a fused protein consisting of a streptavidin-like polypeptide fused end to end with tissue plasminogen activator ("TPA").

Figure 2C:
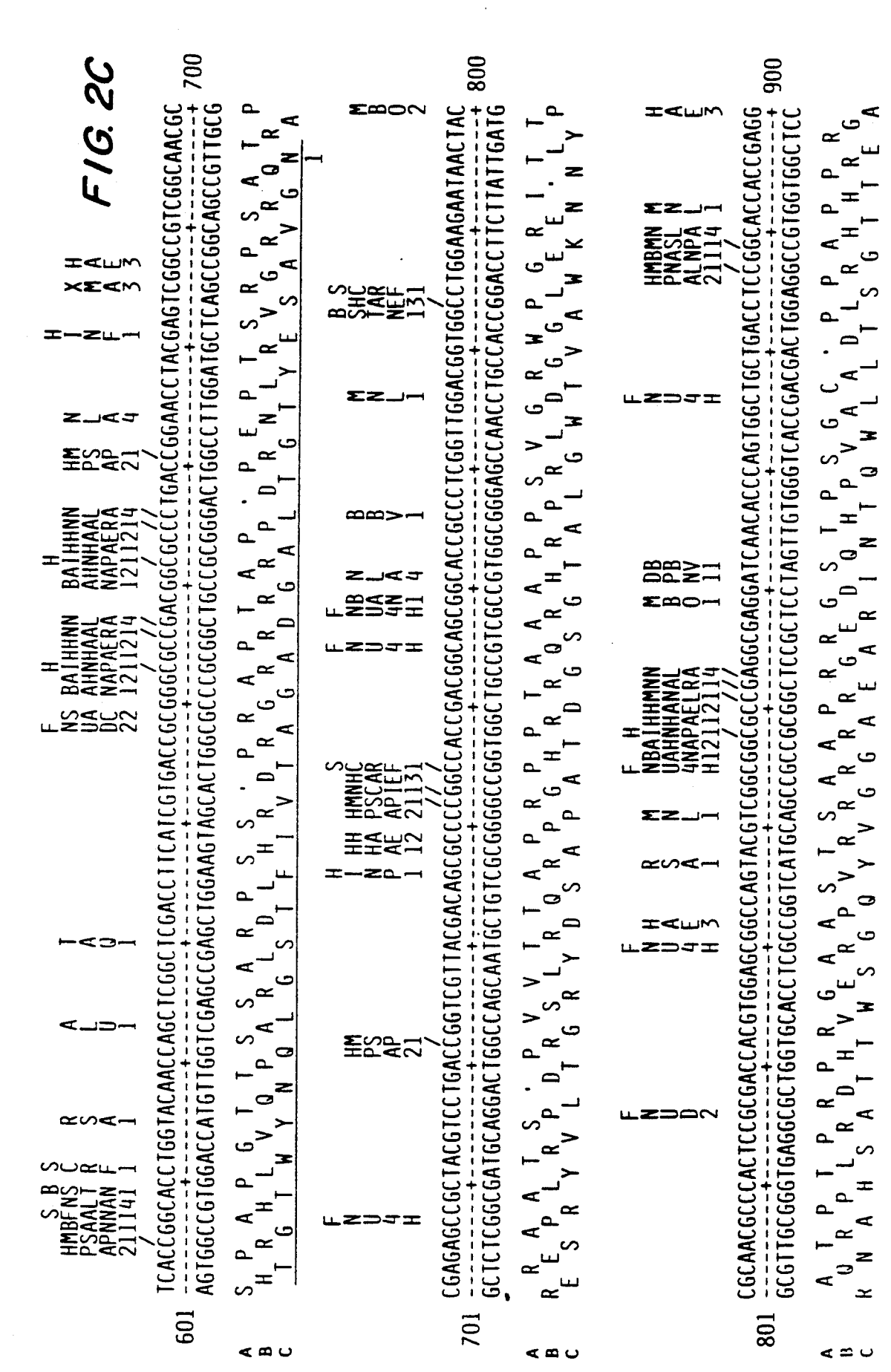
Figure 2D:
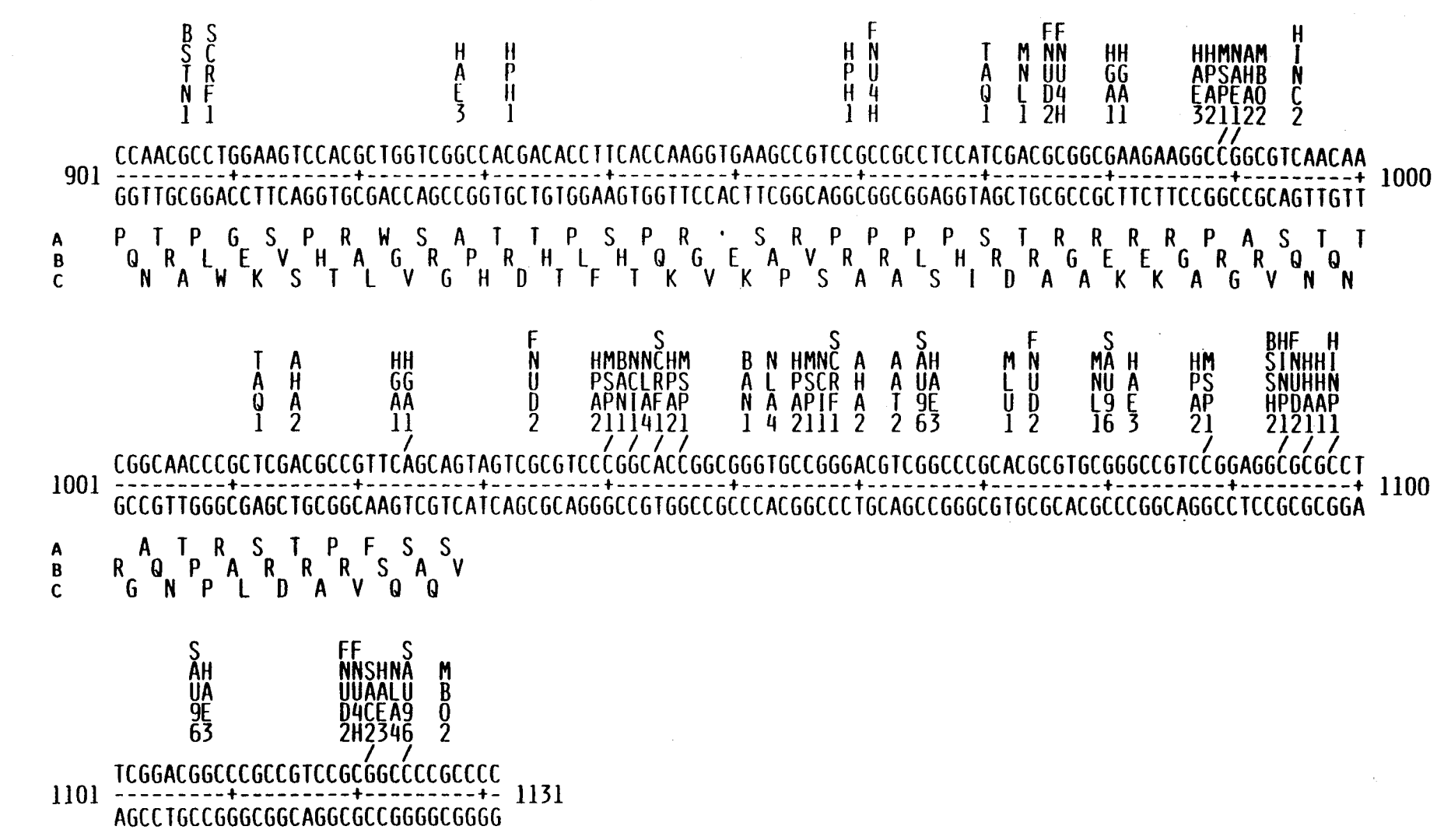
Figure 5:
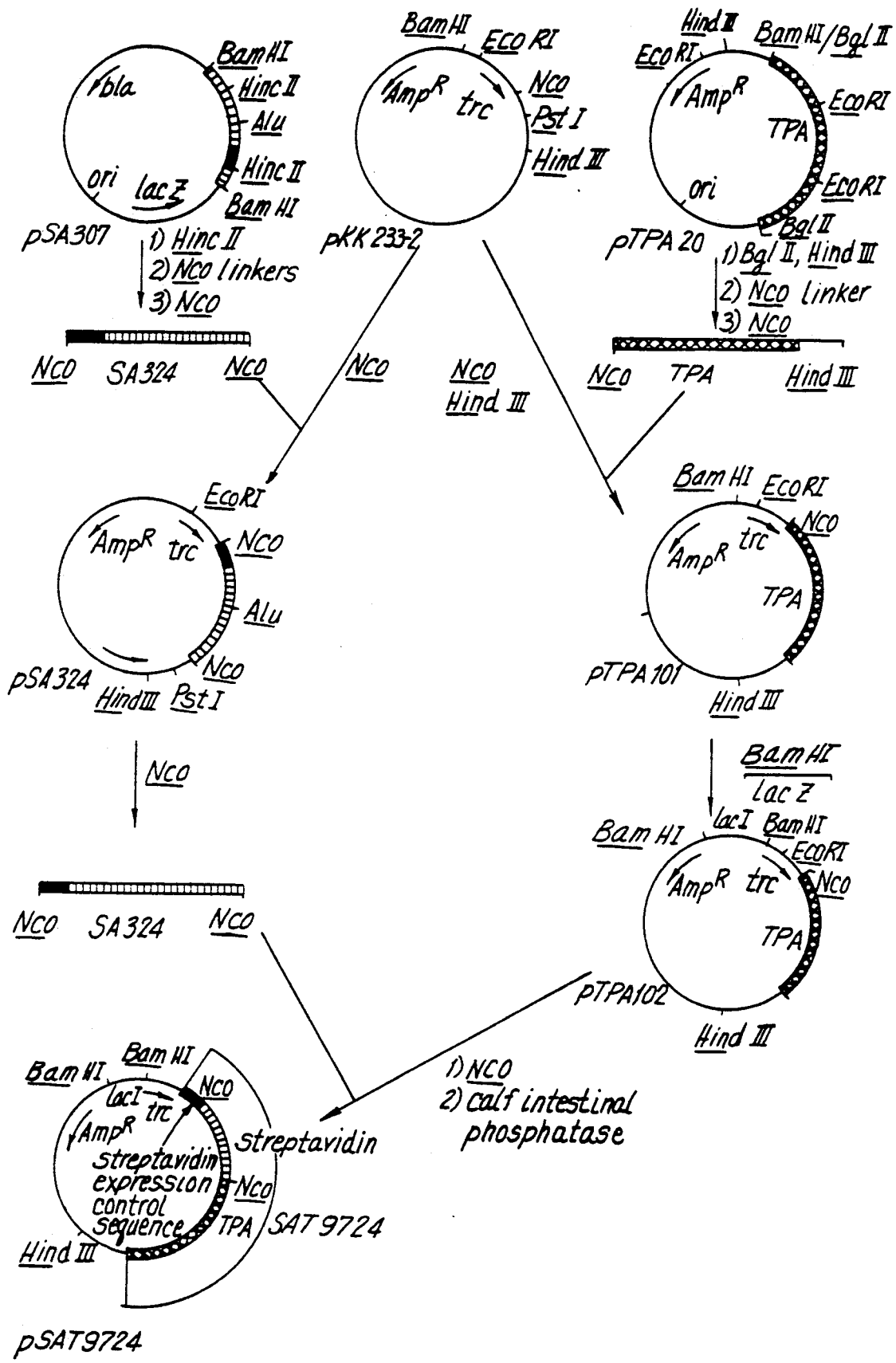
FIG. 5 is a schematic outline of an embodiment of making an expression vector containing DNA sequences encoding a fused streptavidin-like-tissue plasminogen activator protein of this invention.

Referring now to FIG. 5, we first constructed a plasmid containing DNA sequences encoding a streptavidin-like polypeptide. We treated pSA307 with HincII which cuts at nucleotide numbers 174 and 994 within SA307 (FIG. 2). We next added Nco linkers to both ends of this fragment and cut with Nco to create cohesive ends. We designated this fragment SA324.

We then linearized plasmid pKK233-2 (J. Brosius, personal communication) with Nco. We ligated the linearized pKK233-2 to SA324 to produce plasmid pSA324. We transformed *E. coli* K12 cells with pSA324 and cultured the transformed host cells to produce and secrete through the host cell membrane, a streptavidin-like polypeptide. Production of the streptavidin-like polypeptide was induced by IPTG. From this we concluded that pSA324 contains DNA sequences encoding a streptavidin-like polypeptide, including its signal DNA sequence, operatively linked to the TRC expression control sequence present on pKK233-2.

We next constructed a plasmid containing sequences encoding TPA. Plasmid pTPA20 contains a DNA sequence encoding mature TPA inserted between a BglII restriction site at the 3' end and a HindIII restriction at the 5' end of the TPA gene. We treated pTPA20 with BglII and HindIII and isolated the TPA fragment. We ligated an Nco-BglII linker to the 5' end of the TPA gene. We next treated pKK233-2 with Nco and HindIII. We isolated the large fragment and ligated it to the TPA fragment ("pTPA101"). We next cut pTPA101 with BamHI and inserted a fragment containing the lacI (TRC repressor) gene.* We designated this plasmid pTPA102.

* The lacI gene codes for the repressor of the TRC promoter. In the presence of the lacI repressor the TRC promoter will only initiate transcription upon addition of an inducer such as IPTG, thus, enabling us to turn transcription on or off by controlling the level of IPTG added to the host cell.

We constructed the hybrid streptavidin-TPA DNA sequence as follows. We treated pSA324 with Nco to isolate SA324. We next linearized pTPA102 with Nco and treated with calf intestinal phosphatase to prevent recircularization. We ligated the linearized pTPA102 to SA324. We designated this plasmid pSAT9724 and the hybrid DNA sequence SAT9724 present therein.

We transformed *E. coli* HB101 with pSAT9724 and cultured the transformed host. We tested for production of a fused streptavidin-like-TPA protein using the immunological assay described above (H. Towbin et al., *Proc. Natl. Acad. Sci. USA* 76, 4350-54 (1979)). We found that the transformed *E. coli* produced a polypeptide which contained both streptavidin and TPA immunologically reactive material. The protein had an apparent molecular weight of approximately 80,000 daltons. This is consistent with the molecular weight of a fused streptavidin-TPA protein. Production of the fused protein was induced by IPTG, indicating that the hybrid DNA sequence was under the control of the TRC promoter present on pKK233-2.

We next constructed a plasmid which is able to replicate in *S. lividans*. We cut pSAT9724 with BamHI and ligated it to pIJ702 which had been linearized with BglII to form cointigrant plasmids pSAT9786 and pSAT9790. These plasmids are used to transform *S. lividans* which is then cultured to produce and secrete into the cell medium a fused protein consisting of a streptavidin-like polypeptide joined end to end with TPA.

In yet another embodiment of this invention, we constructed a recombinant DNA molecule containing a hybrid DNA sequence which produced a fused protein, consisting of a streptavidin-like polypeptide fused end to end with TPA, only in Streptomyces.

Figure 6:
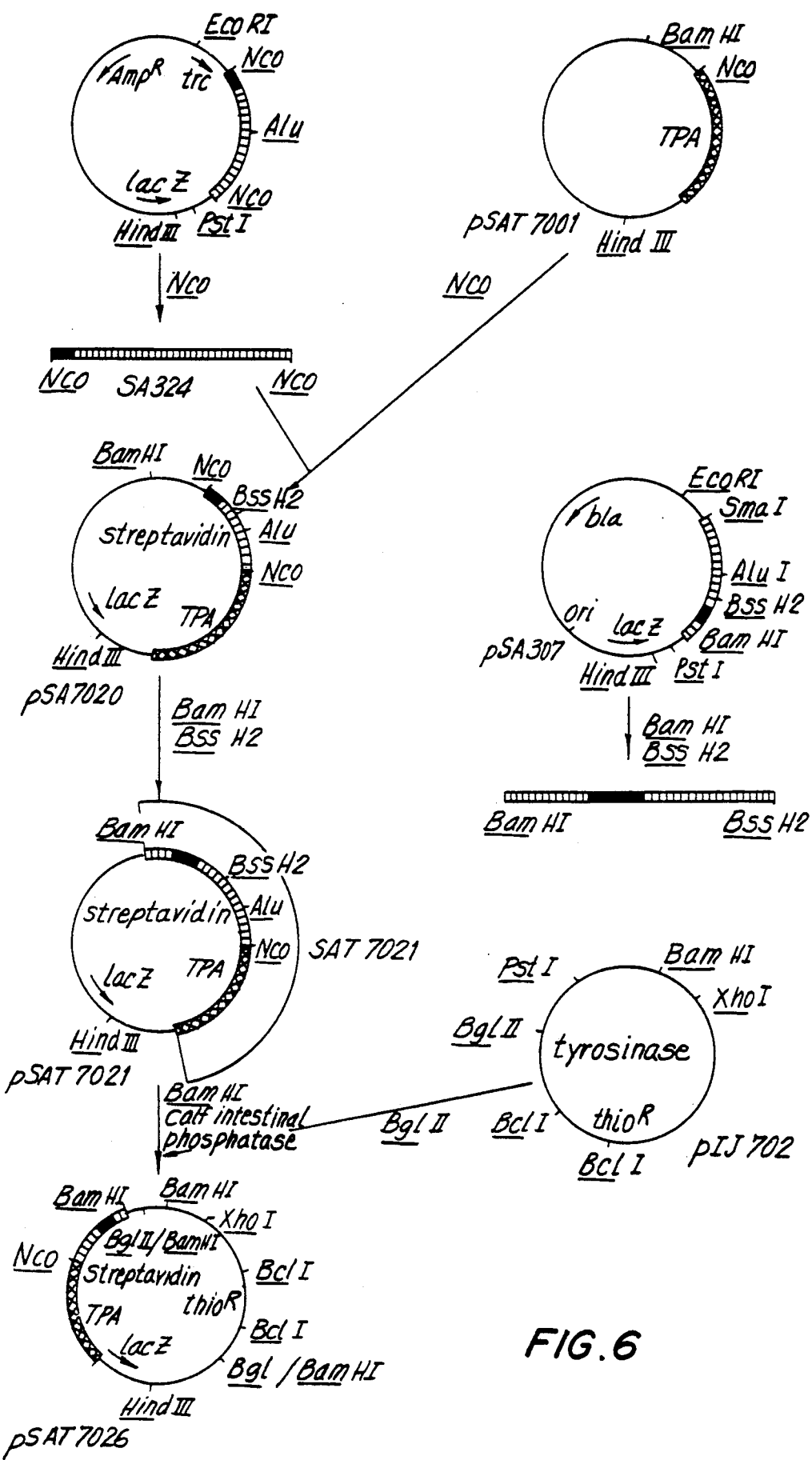
FIG. 6 is a schematic outline of another embodiment of making an expression vector containing DNA sequences encoding a fused streptavidin-like-tissue plasminogen activator protein of this invention.
Figure 7:
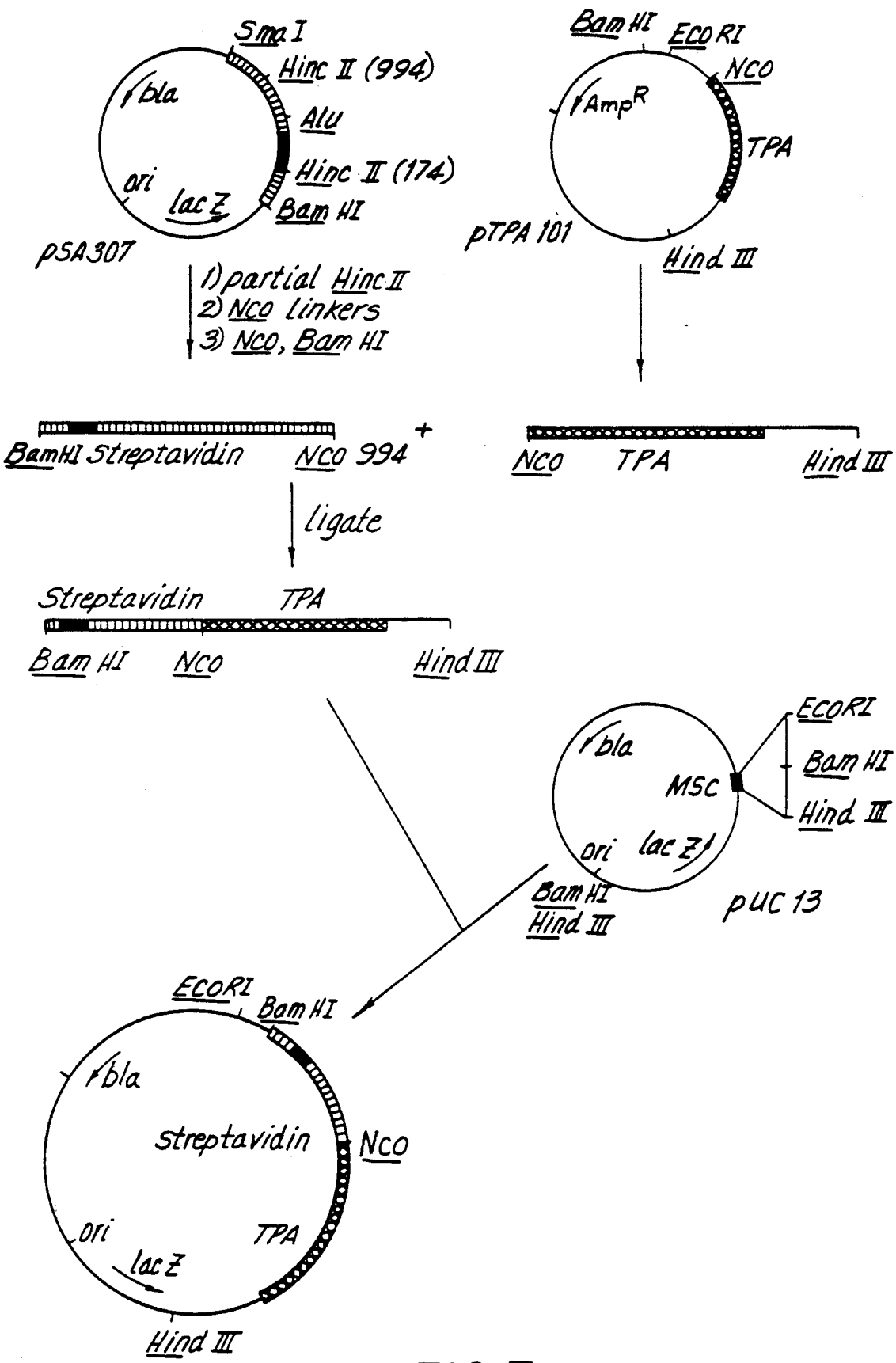
FIG. 7 is a schematic outline of yet another embodiment of making an expression vector containing DNA sequences encoding a fused streptavidin-like-tissue plasminogen activator protein.

Referring now to FIG. 6, we treated pSA324 with Nco and reisolated SA324 containing the DNA sequence encoding a streptavidin-like polypeptide. We linearized pSAT7001, which contains the DNA sequence encoding TPA, with Nco, which cuts in front of the TPA gene, and ligated it to SA324. We isolated plasmid pSAT7020. We confirmed by nucleotide sequencing that the streptavidin gene was in the proper orientation in front of the TPA gene to form a hybrid DNA sequence encoding a fused protein consisting of a streptavidin-like polypeptide joined end to end with TPA.

In order to reconstruct the first 174 nucleotides of SA304 removed upon construction of SA324, we treated pSA307 with BamHI and with BssH2, which cleaves at nucleotide 422 of SA304 (see FIG. 2). We isolated the small fragment. We next treated pSAT7020 with BamHI and BssH2 and ligated the large fragment to the small pSA304 fragment. We designated the resultant plasmid pSAT7021 and the hybrid DNA sequence SAT7021 present therein.

We next linearized pSAT7021 with BamHI and treated the linearized plasmid with calf intestinal phosphatase to prevent recircularization. We ligated BglII-linearized pIJ702 to the linearized pSAT7021 to create a cointegrant plasmid pSAT7026 containing the hybrid streptavidin-TPA DNA sequence. We transformed S. lividans cells with pSAT7026. We isolated from the cell medium a fused protein, containing, immunological activity, as determined by the assay described above, of both streptavidin and TPA.

Although we constructed pSAT7021 as described, a similar plasmid could be more easily constructed as follows. Referring now to FIG. 7, we cleave pSA307 with HincII under conditions in which there is only partial HincII cleavage. We add Nco linkers and cleave with Nco and BamHI. We isolate the 994 nucleotide fragment containing most of the streptavidin gene. We cleave pTPA101 with Nco and HindIII and isolate the DNA fragment encoding TPA. We ligate the two fragments together to produce a hybrid DNA sequence consisting of the streptavidin gene joined end to end with, and in the same reading frame as, the TPA gene. We next cleave pUC13 with BamHI and HindIII and ligate the large fragment to the hybrid DNA sequence. This produced a plasmid containing the hybrid streptavidin-TPA gene under the control of the streptavidin expression control sequence. This plasmid can then be used to form a cointegrant plasmid able to replicate in Streptomyces.

We next isolate secreted proteins from the cell medium using standard techniques [e.g., ammonium sulfate precipitation] and subject the isolate to imminobiotin-agarose column chromatography as described above to separate the fused protein from any contaminant proteins. We elute the fused protein from the imminobiotin-agarose with high ph-urea buffer as described supra and cleave the streptavidin-like polypeptide from the selected protein, polypeptide, peptide or amino acid using a known technique in a manner that does not cleave within either the streptavidin or the selected protein or polypeptide. For example, if the desired protein does not include a methionine, cyanogen bromide may be employed as a cleavage agent. Other methods of protein cleavage have been described supra and may be used in the processes of this invention.

We then separate the streptavidin-like polypeptide from the selected protein, polypeptide, peptide or amino acid by various means, preferably using imminobiotin-agarose column chromatography. The selected protein, polypeptide, peptide or amino acid passes through the column without binding to the imminobiotin and the streptavidin-like polypeptide is eluted from the column as above. If the streptavidin-like polypeptide and the selected protein, polypeptide, peptide or amino acid are of sufficiently different molecular weights, they may also be separated by one of several sizing techniques known in the art such as native polyacrylamide gel electrophoresis or molecular sieve chromatography.

Microorganisms containing the recombinant DNA molecules of this invention are exemplified by cultures deposited in the American Type Culture Collection, Rockville, Md. and identified as follows. Three cultures were deposited on Sep. 10, 1984:

*E. coli* K12, strain JM83 (pSA304)
*E. coli* K12, strain JM83 (pSA307)
*S. lividans* (pSA3721). These cultures have been assigned Accession Numbers 39,845, 39,846 and 39,844, respectively.

Two cultures were deposited on Sep. 26, 1985:

*E. coli* HB101 (pSAT9724)
*S. lividans* (pSAT7026).

These cultures have been assigned Accession Numbers 39,880, and 39,879, respectively.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A fused protein which is produced by a host transformed with a recombinant DNA molecule comprising a hybrid DNA, the hybrid DNA coding for the fused protein and comprising at least two DNAs joined end to end and in the same reading frame, the first DNA coding for streptavidin or a portion thereof, the streptavidin or portion thereof being able to bind to biotin or biotin derivatives or analogues and selected from the group consisting of:

(a) SA304, SA307, SA324;

(b) DNA which hybridizes to any of the foregoing DNA in 6XSSC and 0.1% SDS at 30° C. overnight and which codes on expression for a polypeptide which is able to bind to biotin or biotin derivatives or analogues; and (c) DNA which, within the degeneracy of the genetic code, encodes the same polypeptide as either (a) or (b); and said second DNA coding for another protein, polypeptide, peptide or amino acid.

2. A fused protein, according to claim 1, wherein the protein, polypeptide, peptide or amino acid encoded by the second DNA sequence is selected from the group consisting of human and animal interferons, human and animal growth hormones, antigens of FMDV, antigens of HBV, human insulin, human blood factors, tissue plasminogen activator and erythropoietin.

3. The fused protein according to claim 1, wherein the hybrid DNA further comprises a sufficient protein of a signal DNA sequence to cause secretion of the fused protein across the cell membrane of the transformed host.

4. The fused protein according to claim 1 or 3, wherein the hybrid DNA further comprises a sufficient portion of a signal DNA sequence to cause maturation of the fused protein upon secretion of the fused protein across the cell membrane of the transformed host.

5. A streptavidin, or portion thereof, which is able to bind biotin or biotin derivatives or analogues, said streptavidin containing the streptavidin signal sequence or a portion thereof at the amino terminus and being produced by a host transformed with a recombinant DNA molecule comprising a DNA coding for the streptavidin or portion thereof, the DNA selected from the group consisting of:

(a) SA304 and SA307;

(b) DNA sequences which hybridize to any of the foregoing DNA sequences in 6X and 0.1% SDS at 30° C. overnight and which code for the polypeptide or portion thereof, which is able to bind to biotin or biotin derivatives or analogues; and (c) DNA which, within the degeneracy of the genetic code, encodes the same polypeptide as either (a) or (b).

* * * * *

UNITED STATES PATENT AND TRADEMARK OFFICE
CERTIFICATE OF CORRECTION

PATENT NO. : 5,272,254                     Page 1 of 3
DATED      : December 21, 1993
INVENTOR(S): Meade et al.

It is certified that error appears in the above-indentified patent and that said Letters Patent is hereby corrected as shown below:

On title page, item [56] col. 2, line 16, "nitrocoellulose" should be --nitrocellulose--.

Col. 2,   line 20, Delete hyphen between "the-steps" to --the steps--.

Col. 5,   line 6, ("u") should be upper case --("U");

line 60, "MRNA" should be --mRNA--;

line 66, "MRNA" should be --mRNA--;

line 67, "MRNA" should be --mRNA--.

Col. 6,   line 4, "MRNA" should be --mRNA--;

line 11, "MRNA" should be --mRNA--.

Col. 7,   line 23, "filmentoris" should be --filamentous--;

line 43, After "streptavidin" insert hyphen -- - --.

Col. 9,   line 46, "of-cleaving" should be --of cleaving--.

Col. 10,  line 24, "Biopay" should be --Biophys--.

Col. 11,  line 22, "(50pg/ml)" should be --(50µg/ml)--;

line 37, "Grüstein" should be --Grünstein--;

line 37, "Hogess" should be --Hogness--;

UNITED STATES PATENT AND TRADEMARK OFFICE
CERTIFICATE OF CORRECTION

PATENT NO. : 5,272,254  Page 2 of 3
DATED : December 21, 1993
INVENTOR(S) : Meade et al.

It is certified that error appears in the above-indentified patent and that said Letters Patent is hereby corrected as shown below:

line 52, "pUCs" should be --pUC8--;

Col. 11,  line 55, "pUCs" should be --pUC8--;

line 63, "pUCs" should be --pUC8--.

Col. 12,  line 36, "pUCs" should be --pUC8--.

Col. 13,  line 6, "iminobiotin" should be --imminobiotin--;

line 16, After "biotin" insert hyphen -- - --;

line 21, "iminobiotin" should be --imminobiotin--.

Col. 14,  line 41, "Si" should be --S1--.

Col. 18,  line 4, "1985" should be --1984--;

line 38, After "DNA" delete --sequence--;

UNITED STATES PATENT AND TRADEMARK OFFICE
CERTIFICATE OF CORRECTION

PATENT NO. : 5,272,254
DATED : December 21, 1993
INVENTOR(S) : Meade et al.

It is certified that error appears in the above-indentified patent and that said Letters Patent is hereby corrected as shown below:

Column 18, line 61, after "6X" insert --SSC--.

Signed and Sealed this

Sixteenth Day of August, 1994

Attest:

BRUCE LEHMAN

Attesting Officer   Commissioner of Patents and Trademarks